United States Patent
Holmes et al.

(10) Patent No.: US 12,239,490 B2
(45) Date of Patent: Mar. 4, 2025

(54) ULTRASOUND IMAGING SYSTEM WITH TISSUE SPECIFIC PRESETS FOR DIAGNOSTIC EXAMS

(71) Applicant: KONINKLIJKE PHILIPS N.V., Eindhoven (NL)

(72) Inventors: Anne Holmes, Bothell, WA (US); Martin Stumpf, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/223,609

(22) Filed: Jul. 19, 2023

(65) Prior Publication Data
US 2023/0355214 A1    Nov. 9, 2023

Related U.S. Application Data

(62) Division of application No. 16/959,495, filed as application No. PCT/EP2019/050019 on Jan. 2, 2019, now Pat. No. 11,744,557.

(60) Provisional application No. 62/613,077, filed on Jan. 3, 2018.

(51) Int. Cl.
*A61B 8/08* (2006.01)
*A61B 8/00* (2006.01)

(52) U.S. Cl.
CPC ............ *A61B 8/5246* (2013.01); *A61B 8/08* (2013.01); *A61B 8/461* (2013.01); *A61B 8/488* (2013.01); *A61B 2560/0487* (2013.01)

(58) Field of Classification Search
CPC .............................. A61B 8/5246; A61B 8/488
See application file for complete search history.

(56) References Cited

U.S. PATENT DOCUMENTS

| 5,315,999 A * | 5/1994 | Kinicki .............. G01S 7/52073 600/443 |
| 2014/0180106 A1 | 6/2014 | Takahashi et al. |
| 2016/0338676 A1* | 11/2016 | Berger ................... G16H 20/40 |

FOREIGN PATENT DOCUMENTS

| WO | 03027662 A2 | 4/2003 |
| WO | 2010055820 A1 | 5/2010 |

OTHER PUBLICATIONS

International Search Report for International Application No. PCT/EP2019/050019, filed Jan. 2, 2019, 13 pages.

* cited by examiner

*Primary Examiner* — Joel Lamprecht
*Assistant Examiner* — Nyrobi Celestine

(57) ABSTRACT

An ultrasound system has user selectable tissue specific presets by which a user can condition the ultrasound system to be optimized for specific types of diagnostic exams. After an exam type has been selected and the exam commenced, a user manipulates imaging and workflow controls to better visualize the target anatomy. The user has the choice of setting up the system so that imaging and workflow settings are maintained when the tissue specific presets are changed, or to reset the imaging and workflow settings to default values upon a change of the tissue specific presets.

4 Claims, 5 Drawing Sheets

ULTRASOUND IMAGING SYSTEM WITH TISSUE SPECIFIC PRESETS FOR DIAGNOSTIC EXAMS

RELATED APPLICATIONS

This application is a divisional application of U.S. patent application Ser. No. 16/959,495, filed on Jul. 1, 2020, which in turn is the U.S. National Phase application under 35 U.S.C. § 371 of International Application No. PCT/EP2019/050019, filed on Jan. 2, 2019, which claims priority to and the benefit of U.S. Provisional Application Ser. No. 62/613,077, filed Jan. 3, 2018. These applications are hereby incorporated by reference herein.

This invention relates to medical diagnostic ultrasound systems and, in particular, to ultrasound systems with preset values for diagnostic parameters for specific types of exams, referred to herein as tissue specific presets.

Setting up an ultrasound system for a particular type of diagnostic imaging exam typically entails adjusting numerous controls and settings of the ultrasound system. For example, the user can set the imaging mode, the depth in the body to be displayed in the image, and adjust the focus at that depth. The frame rate of display is another parameter that can be adjusted, often by varying the maximum image depth or image width. For cardiac exams the user may turn on and adjust the settings of color or spectral Doppler, such as color box placement and the frequency range of blood flow; blood flow in the heart will be at a greater velocity than venous flow, for instance. More subtle parameters such as the cutoff of the wall filter during blood flow exams may also be adjusted. There are literally scores of such parameters that may be adjusted on a typical ultrasonic imaging system.

Since it can take a considerable amount of time for a sonographer to set up an ultrasound system for a particular exam type, one of the earliest advances in system technology was to enable a sonographer to save the parameters used for a particular exam. When the sonographer would later perform the same type of exam with a different patient, the saved parameter values could be recalled and invoked for the new exam. See, for instance, U.S. Pat. No. 5,315,999 (Kinicki et al.) Multimodality ultrasound systems, systems capable of performing cardiology as well as radiology exams, now come with factory-installed initial parameter settings for both cardiac and general imaging exams. Factory-installed presets then became more specialized. Special preset packages became available not just for all abdominal exams, but different groups of presets could be invoked for different abdominal exams, such as a liver exam or an obstetrical exam. These packages of presets became known as tissue specific presets, as each one would optimize system operating parameters for diagnosis of a specific anatomy or organ of the body, such as a heart, liver, or fetus. Today, groups of tissue specific presets have become even more specialized. Ultrasound systems available from Philips Medical Systems of Andover, MA, for example, enable a user to invoke presets particular to an OB exam, such as "OB Gen" presets, and also parameter presets for even more specialized subsets of an OB exam such as "OB Fetal Heart" presets and "OB Fetal Echo" presets. But when a new group of preset parameters in invoked, the effect on the ultrasound system can be similar to commencing a new exam. Display and workflow settings made when using a previous set of preset values can be reset to default values, requiring their adjustment again by the user. While some of the settings may no longer be applicable to the new imaging mode, others may retain their usefulness with the new tissue specific presets. It is desirable to enable a user to be able to save display and workflow settings when changing tissue specific presets, so that the user does not have to spend time making adjustments previously made during an exam.

In accordance with the principles of the present invention, an ultrasound system has the capability of maintaining display and workflow settings during an exam when a user invokes a new group of tissue specific presets. The system can be controlled to save all display and workflow settings from one tissue specific exam to a new one, including those that may be incompatible with the new tissue specific exam, or only those which are compatible or are potentially useful in the newly invoked tissue specific exam. Enabling these display and workflow settings to be maintained can save the time required to reset them, and can make possible views of a subject requiring speed and diagnostic agility.

Figure 3A:
Figure 3B:
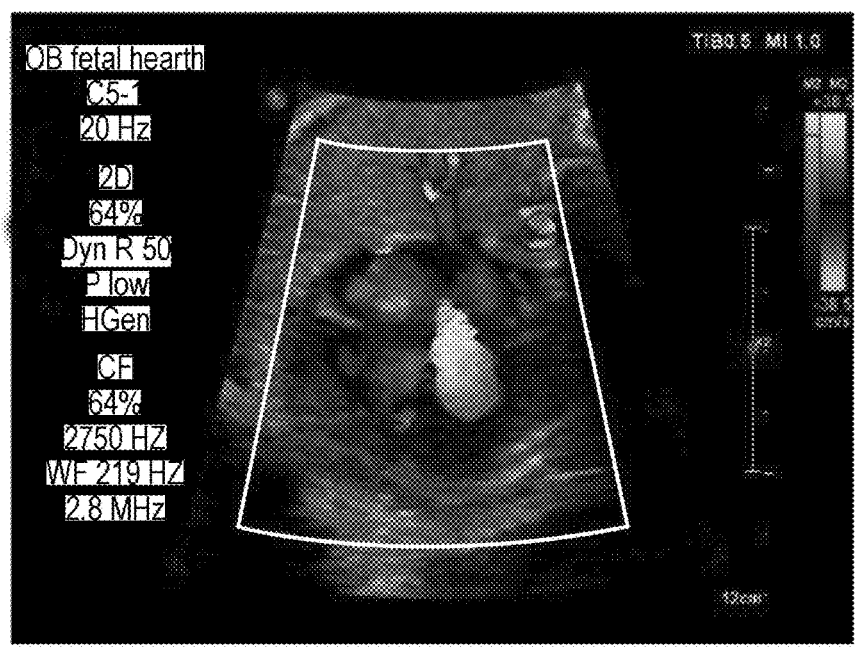
Figure 3C:
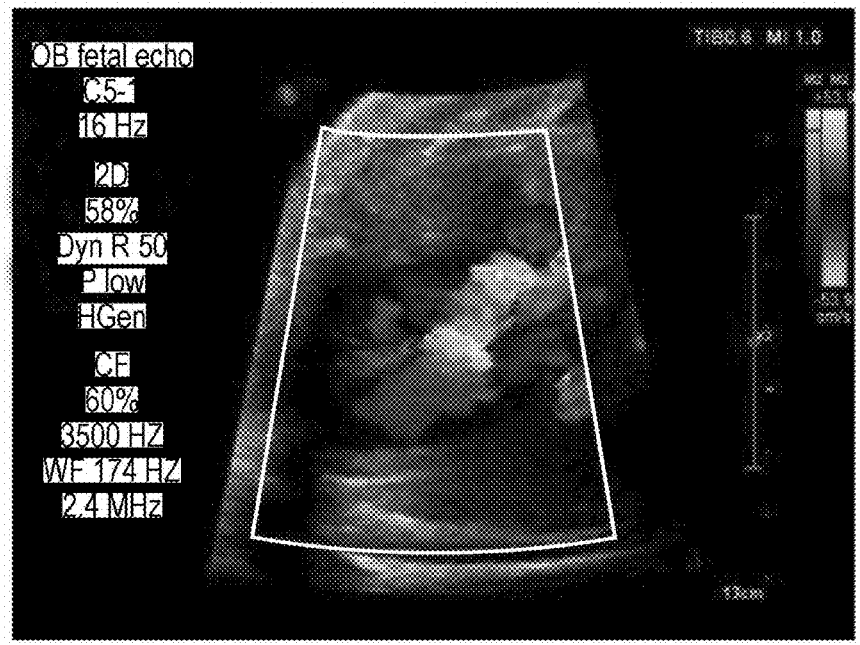

FIGS. 3*a*, 3*b* and 3*c* illustrate ultrasound images acquired when using three different sets of tissue specific presets during an OB exam.

Figure 4:
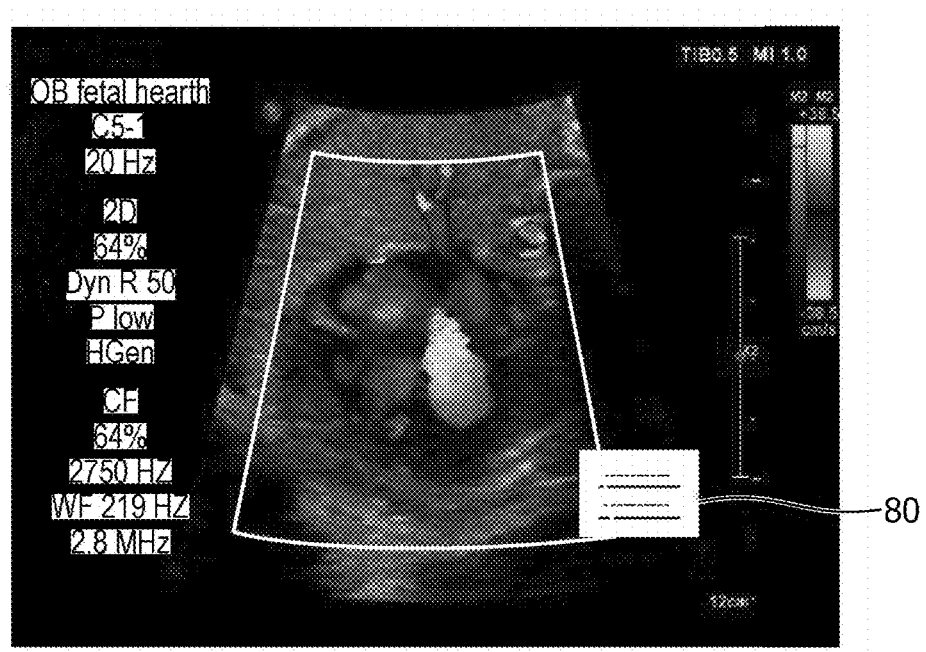

FIG. 4 illustrates an ultrasound image display with a pop-up control settings box that appears at a change of TSP mode.

Figure 4A:
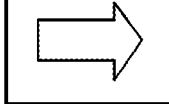

FIG. 4*a* is an enlarged view of an exemplary pop-up control settings box.

Figure 1:
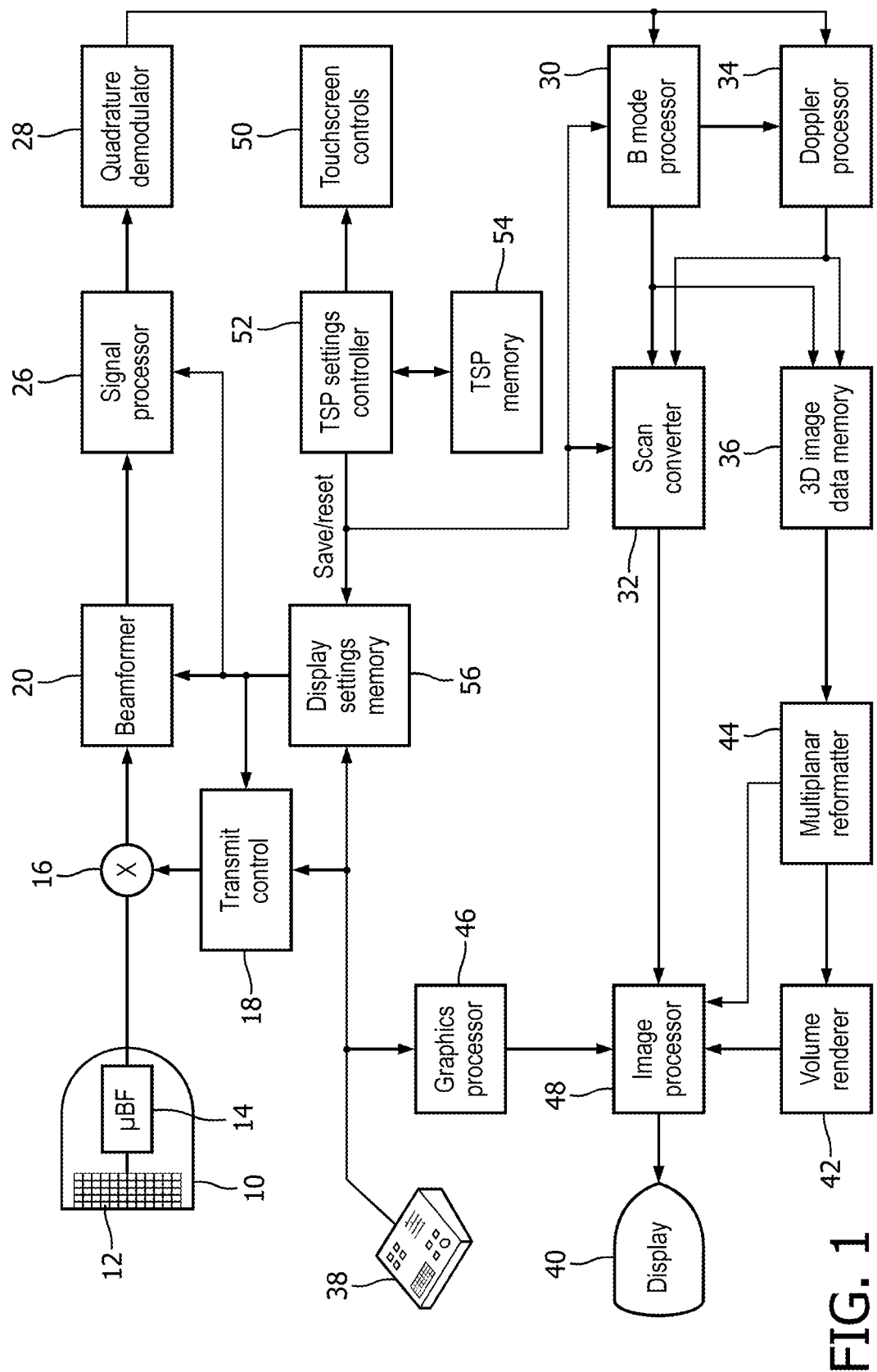
FIG. 1 illustrates in block diagram form an ultrasound system configured in accordance with the principles of the present invention.

Referring now to FIG. 1, an ultrasonic diagnostic imaging system constructed in accordance with the principles of the present invention is shown in block diagram form. A transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. The transducer array 12 is coupled to a microbeamformer 14 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 12 under control of the microbeamformer 14 is directed by a transmit controller 18 coupled to the T/R switch and the beamformer 20, which receives input from the user's operation of the user interface or control panel 38. Among the transmit characteristics controlled by the transmit controller are the number, spacing, amplitude, phase, and polarity of transmit waveforms. Beams formed in the direction of pulse transmission may be steered straight ahead from the transducer array, or at different angles for a wider sector field of view.

The echoes received by a contiguous group of transducer elements are beamformed by appropriately delaying them and then combining them. The partially beamformed signals produced by the microbeamformer 14 from each patch are coupled to a main beamformer 20 where partially beamformed signals from individual patches of transducer elements are combined into a fully beamformed coherent echo signal. For example, the main beamformer 20 may have 128 channels, each of which receives a partially beamformed signal from a patch of 12 transducer elements. In this way the signals received by over 1500 transducer elements of a two-dimensional array transducer can contribute efficiently to a single beamformed signal.

The coherent echo signals undergo signal processing by a signal processor 26, which includes filtering by a digital filter and noise reduction as by spatial or frequency compounding. The signal processor can also shift the frequency band to a lower or baseband frequency range. The digital filter of the signal processor 26 can be a filter of the type disclosed in U.S. Pat. No. 5,833,613 (Averkiou et al.), for example. The processed echo signals then are demodulated by a quadrature demodulator 28 into quadrature (I and Q) components, which provide signal phase information.

The beamformed and processed coherent echo signals are coupled to a B mode processor 30 which produces a B mode image of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 34. The Doppler processor 34 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For a color Doppler image, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format or a sector display format. Either the B mode image or the Doppler image may be displayed alone, or the two shown together in anatomical registration in which the color Doppler overlay shows the blood flow in tissue and vessels in the image as shown in FIGS. 3a-3c. Another display possibility is to display side-by-side images of the same anatomy which have been processed differently. This display format is useful when comparing images.

The image data produced by the B mode processor and the Doppler processor 34 are coupled to a 3D image data memory 36, where it is stored in memory locations addressable in accordance with the spatial locations from which the image values were acquired. A multiplanar reformatter 44 converts echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 3D images and 2D images produced by the scan converter 32, the multiplanar reformatter 44, and the volume renderer 42 are coupled to an image processor 48 for further enhancement, buffering and temporary storage for display on an image display 40. A graphic display overlay containing textual, parametric, and other graphic information such as patient ID is produced by a graphics processor 46 and coupled to the image processor for display with the ultrasound images.

Figure 2:
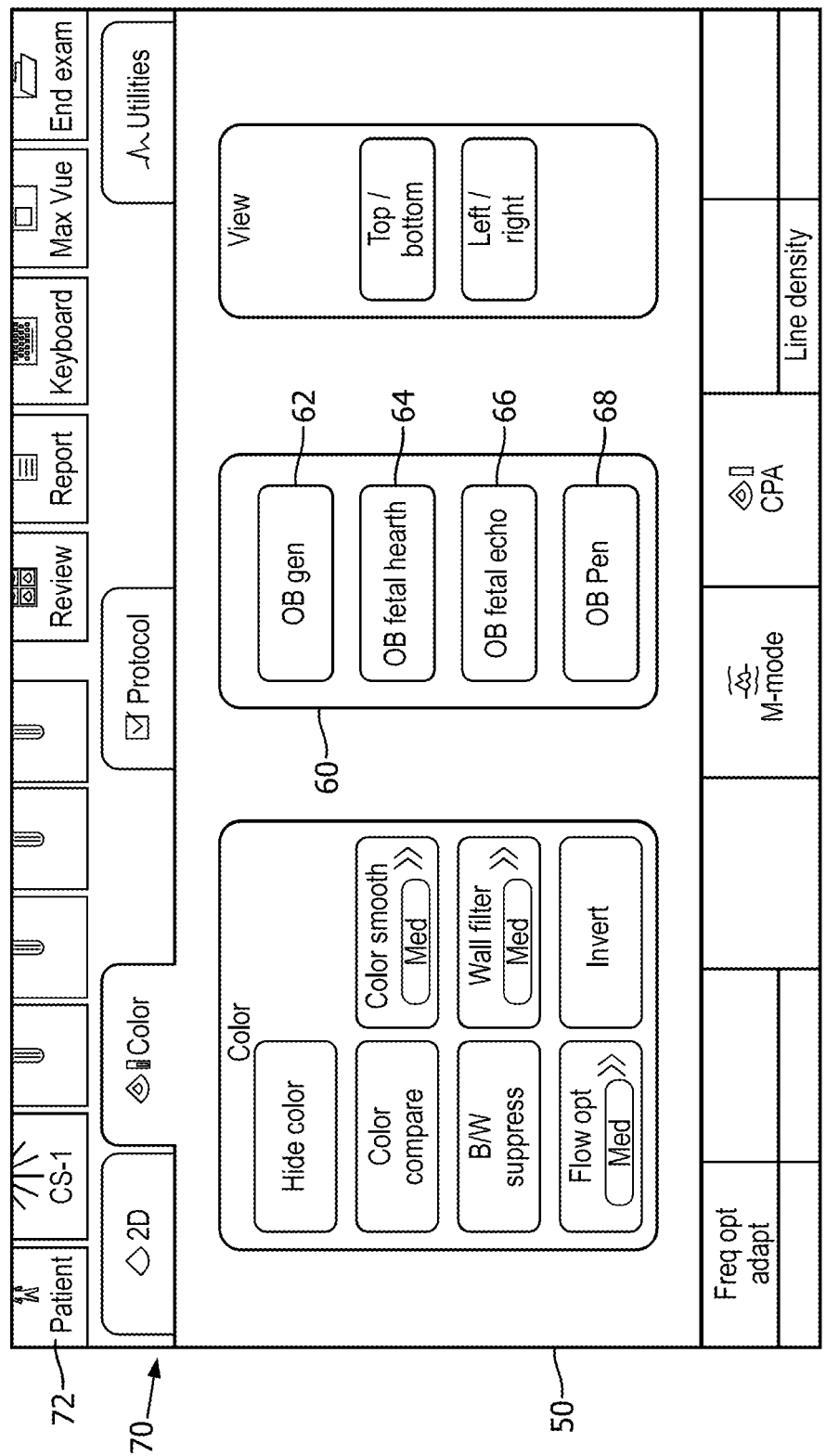
FIG. 2 illustrates a touchscreen ultrasound system control panel suitable for use with an implementation of the present invention.

In the implementation of FIG. 1 the user interface controls also comprise a touchscreen control panel 50 as shown in FIG. 2. The central display area of the touchscreen display has a number of tabs 70 such as 2D and Color which the user can select to choose an imaging mode. In the illustration the Color panel has been selected. In the center of the panel is a display area 60 of tissue specific presets (TSPs) which the user can select for a particular type of exam. In this example the display area 60 is displaying buttons 62-68 for four different obstetrical (OB) exam types. By touching or clicking on one of the buttons with a pointing device such as a mouse or trackball, the ultrasound system is conditioned to operate with parameters optimized for the particular exam type. For instance, when the user touches button 62 to conduct a general OB exam ("OB Gen"), a command for an OB Gen exam is applied to a TSP settings controller 52 in the ultrasound system (see FIG. 1). This TSP will cause the system to operate with a relatively low (e.g., 16 Hz) frame rate of display by control of the transmit controller and beamformer and a relatively high dynamic range of display. When color is turned on to show blood flow, a relatively low range of flow velocities is depicted by the color values such as ±24 cm/sec. Doppler sample rate is set to a relatively low value such as 1.7 kHz and the wall filter of the Doppler processor is set to a relatively low cutoff frequency of just over 100 Hz. An exemplary OB Gen image with the color turned on is illustrated in FIG. 3a.

When the user touches button 64 to select an OB Fetal Heart exam, the tissue specific preset values are optimized for this slightly different and more specific exam. The frame rate is increased to capture the rapid beating of a fetal heart, such as 20 Hz or higher. The dynamic range is decreased slightly and color is automatically turned on by the TSP to show a greater range of blood flow velocities such as ±38 cm/sec. The Doppler sample rate is increased to a higher value such as 2.7 kHz and the wall filter cutoff is increased to a frequency of over 200 Hz. These TSP settings optimize the system operation for imaging the fetal heart. An exemplary OB Fetal Heart image is illustrated in FIG. 3b.

When the user touches button 66 to select an OB Fetal Echo exam, the tissue specific preset values are again optimized, this time to operating parameters preferred by pediatric cardiologists. The frame rate is decreased slightly to 16 Hz. The dynamic range remains the same as the OB Fetal Heart mode and color is automatically turned on by the TSP to show an even greater range of blood flow velocities such as ±54 cm/sec. The Doppler sample rate is increased even further to a sampling rate such as 3.6 kHz and the wall filter cutoff is decreased to a frequency of about 170 Hz. These TSP settings optimize the system operation for conduct of a fetal echo exam. An exemplary OB Fetal Echo image is illustrated in FIG. 3c.

Other system parameters which may be optimized by a set of TSPs include the color persistence (the decay rate of color pixels), color write priority (whether to display an ambiguous pixel as grayscale or color), color gain, grayscale dynamic range, and grayscale mapping.

While the sometimes-subtle differences of these TSP settings may not be readily apparent from the drawing figures, the visual differences in the color performance in the central areas of the three images illustrate the distinctiveness of these three OB imaging TSPs. The fourth TSP button 68 in the display panel of FIG. 2 is for deep penetration during OB imaging ("OB Pen"), and that TSP will increase the probe transmit power and decrease the frame rate for scanning deeper depths in the body. The changes in operation effected by different system TSPs are controlled by the TSP settings controller 52, which is seen coupled to various processors and controllers of the ultrasound system to implement the necessary changes in system operating parameters. When a touchscreen button is selected for a specific TSP, the TSP settings controller accesses the desired TSP values from a TSP memory 54, then applies the preset values to the appropriate ultrasound system processors and controllers.

As the user is conducting an exam in a selected TSP mode of operation, he or she is continually actuating display controls on the control panel 38 or 50 to best view the target anatomy for diagnosis. For instance, the user may increase or decrease the display depth, widen or narrow the field of view of the image, or adjust the focal point in the image. The user may zoom in to more closely view small anatomical structures such as a fetus, or change the viewing direction of anatomy visualized in 3D. Color may be turned on or off. In accordance with the principles of the present invention these changes in the display settings or exam workflow are stored in a display settings memory 56 and updated as they change. In a typical ultrasound system the display and workflow settings are re-initialized to default values when a TSP mode is changed. Sometimes this reset to default values is useful, as when a completely different exam is to be conducted, e.g., changing from a cardiac exam to a liver exam. But sometimes it is useful to retain the display and workflow settings when display continuity is beneficial. In accordance with a further aspect of the present invention, a user can decide whether to retain or reset these settings when changing TSP modes. A real-life example of an ultrasound exam illustrates the utility of this option.

Suppose that a sonographer is to conduct an obstetrical exam of a developing fetus. A sonographer begins a routine OB exam by selecting the OB Gen TSP by touching touchscreen button 62. As the exam progresses the sonographer captures required images of the head, abdomen, leg bones, and arm bones. Then the fetus moves in the uterus and turns chest up such that the heart is in the perfect position for interrogation. The sonographer quickly reduces the depth and sector width, adjusts the focal zone location, turns on and positions the HD Zoom box, and then turns on color. It is at this point the sonographer realizes he is using the TSPs for the OB Gen mode and remembers that the ultrasound system is better optimized for visualizing flow in the heart when operating with the TSPs of the OB Fetal Heart mode. The sonographer thus selects the OB Fetal Heart TSPs by touching button 64—but now the image settings are back to default values: no color, full sector size, no HD Zoom, and so forth. He must then adjust the display settings to all the previously set values before he can see the optimized color in the heart, hoping the baby does not move again while he adjusts the image and workflow settings.

An implementation of the present invention provides a way to switch between different TSP modes while maintaining the display and workflow changes previously made, such as region size and positions, and image layouts such as color compare. Upon selection of a TSP mode button, a system of the present invention will maintain the current user display and workflow settings, but apply the optimized settings for the TSP mode indicated on the touchscreen button. In the foregoing exemplary scenario, the sonographer would have adjusted his image display to achieve the OB Gen image, then by simply pushing the OB Fetal Heart button he would immediately display the OB Fetal Heart image in the same orientation without have to adjust depth, HD Zoom, or even turning on color; those display settings are maintained. If he wanted to quickly see the differences in color optimization between OB Fetal Heart and OB Fetal Echo, he could rapidly switch between these TSP modes without having to spend time adjusting the display controls.

One way to implement this feature is to present the user at the outset of an exam with a choice of display and workflow settings to maintain or reset during TSP mode changes. The touchscreen control panel of FIG. 2 has a "Patient" button 72, which the user touches at the outset of an exam to enter information about the patient to be examined. In accordance with a further aspect of the present invention, when the user actuates the Patient button 72, he is presented with a choice of system settings. One is to maintain display and workflow settings when changing TSP modes. Another is to reset display and workflow settings to default values when changing TSP modes. Other choices may be to maintain (or reset) display and workflow settings which may be incompatible with a new TSP mode. For example, when a user switches to the OB Gen TSP mode in order to visualize and measure fetal bone sizes, color is generally not turned on, as bones are best visualized in B mode. These latter choices enable a user to decide whether to maintain or reset incompatible settings such as color operation in this example. A user can make these choices in system operation during initial patient setup, which will continue for the duration of the exam. Of course, the user can manually override the effects of these choices during an exam. Continuing the above example, a user may switch to the OB Gen mode to measure fetal bones, and see that the color mode has been maintained from the previous TSP mode. He can then turn it off manually by actuation of the appropriate control on the user interface.

The system drawing of FIG. 1 illustrates the operations of these setup choices. If the user has elected to maintain display and workflow settings when changing TSP modes, the TSP settings controller 52 will issue a "Save" command to the display settings memory 56 when a TSP mode is to be changed. The current display and workflow settings will thus be saved and continue in the new TSP mode. Alternatively, if the user has elected to reset all or incompatible display and workflow settings when the TSP mode is changed, the TSP settings controller 52 will issue a "Reset" (or "Reset Incompatible") command to the display settings memory when the TSP mode is to be changed.

FIGS. 4 and 4a illustrate another implementation of the present invention. In this implementation, when a user touches a TSP button on the touchscreen to change to a new TSP mode, a pop-up box 80 appears on the ultrasound image screen as shown in FIG. 4. The pop-up box 80 is populated with all of the display and workflow control settings that the user adjusted during the previous TSP mode, which have been saved during the procedure in the display settings memory 56. As shown in the enlarged view of the pop-up box 80 in FIG. 4a, the box identifies the controls which have been used in the first column and provides their current settings in the second column. In the third column the user is given the choice of whether to continue a setting in the new TSP mode ("Yes") or to reset it in the new mode ("No"). In the example of FIG. 4a, the user has chosen to keep all but one of the control and workflow settings of the previous TSP mode, and to turn off the Zoom function. After the user is satisfied that he has kept and deleted the settings as desired for the new TSP mode, the user clicks on the arrow 82 at the bottom of the box 80 and the system completes the change to the new TSP mode, including all of the display and workflow settings that the user has chosen to continue using in the new mode.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system, for example, the TSP settings controller or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system or the data network for importing training images. The computer or processor may also include a memory. The memory devices such as the TSP memory 54 and the display settings memory 56 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a neural network model module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound system, the system comprising at least one processor and at least one memory in communication with the processor, the memory storing instructions, when executed by the processor, cause the processor to:
   receive beamformed ultrasound signals;
   generate B-mode and Doppler images from the beamformed ultrasound signals;
   display the generated B-Mode and Doppler images with a first mode of tissue-specific preset (TSP) settings and with one or more non-TSP settings, wherein none of the non-TSP settings are TSP settings;
   receive at least one user input, via a user interface, for control of a plurality of TSP settings, each being specific to a tissue of a person being imaged, and for control of the one or more non-TSP settings;
   adjust, in response to the user input, the TSP settings from the first mode to a second mode while maintaining the non-TSP settings.

2. The ultrasound system of claim 1, wherein the non-TSP settings comprise display and workflow settings.

3. The ultrasound system of claim 2, wherein the display and workflow settings comprise one or more of image size, depth, focal point, and image zoom.

4. The ultrasound system of claim 1, wherein the TSP settings further comprise one or more of settings for flow velocity range, color persistence, color write priority, color gain, transmit power, colorflow, dynamic range, and grayscale mapping.

* * * * *